(12) United States Patent
Mansi et al.

(10) Patent No.: US 9,277,970 B2
(45) Date of Patent: Mar. 8, 2016

(54) SYSTEM AND METHOD FOR PATIENT SPECIFIC PLANNING AND GUIDANCE OF ABLATIVE PROCEDURES FOR CARDIAC ARRHYTHMIAS

(71) Applicants: Tommaso Mansi, Westfield, NJ (US); Olivier Ecabert, Pretzfeld (DE); Saikiran Rapaka, Ewing, NJ (US); Bogdan Georgescu, Plainsboro, NJ (US); Ali Kamen, Skillman, NJ (US); Dorin Comaniciu, Princeton Junction, NJ (US)

(72) Inventors: Tommaso Mansi, Westfield, NJ (US); Olivier Ecabert, Pretzfeld (DE); Saikiran Rapaka, Ewing, NJ (US); Bogdan Georgescu, Plainsboro, NJ (US); Ali Kamen, Skillman, NJ (US); Dorin Comaniciu, Princeton Junction, NJ (US)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 352 days.

(21) Appl. No.: 13/946,661

(22) Filed: Jul. 19, 2013

(65) Prior Publication Data

US 2014/0022250 A1 Jan. 23, 2014

Related U.S. Application Data

(60) Provisional application No. 61/673,407, filed on Jul. 19, 2012.

(51) Int. Cl.
*G06K 9/00* (2006.01)
*A61B 19/00* (2006.01)
(Continued)

(52) U.S. Cl.
CPC ............... *A61B 19/50* (2013.01); *A61N 7/022* (2013.01); *G06T 7/0083* (2013.01); *G06T 7/0089* (2013.01); *G06T 19/20* (2013.01); *A61B 5/042* (2013.01); *A61B 18/02* (2013.01);
(Continued)

(58) Field of Classification Search
None
See application file for complete search history.

(56) References Cited

U.S. PATENT DOCUMENTS 7,668,354 B2   2/2010 O'Donnell et al.
7,715,604 B2 * 5/2010 Sun ...................... A61B 5/0035
                                            382/128

(Continued)

OTHER PUBLICATIONS

Dikici et al., "Quantification of Delayed Enhancement MR Images", In Proc. MICCAI 2004, LNCS 3216, pp. 250-257, 2004.

(Continued)

*Primary Examiner* — Shefali Goradia

(57) ABSTRACT

A method and system for patient-specific planning and guidance of an ablation procedure for cardiac arrhythmia is disclosed. A patient-specific anatomical heart model is generated based on pre-operative cardiac image data. The patient-specific anatomical heart model is registered to a coordinate system of intra-operative images acquired during the ablation procedure. One or more ablation site guidance maps are generated based on the registered patient-specific anatomical heart model and intra-operative patient-specific measurements acquired during the ablation procedure. The ablation site guidance maps may include myocardium diffusion and action potential duration maps. The ablation site guidance maps are generated using a computational model of cardiac electrophysiology which is personalized by fitting parameters of the cardiac electrophysiology model using the intra-operative patient-specific measurements. The ablation site guidance maps are displayed by a display device during the ablation procedure.

45 Claims, 11 Drawing Sheets

(51) Int. Cl.
G06T 19/20 (2011.01)
G06T 7/00 (2006.01)
A61N 7/02 (2006.01)
G06F 19/00 (2011.01)
A61B 18/14 (2006.01)
A61B 5/042 (2006.01)
A61B 18/02 (2006.01)
A61N 1/362 (2006.01)
A61B 18/00 (2006.01)
A61N 1/39 (2006.01)

(52) U.S. Cl.
CPC ... *A61B 18/1492* (2013.01); *A61B 2018/00357* (2013.01); *A61B 2018/00577* (2013.01); *A61B 2018/00839* (2013.01); *A61B 2019/504* (2013.01); *A61B 2019/505* (2013.01); *A61B 2019/507* (2013.01); *A61B 2019/5242* (2013.01); *A61B 2019/5289* (2013.01); *A61N 1/362* (2013.01); *A61N 1/39* (2013.01); *G06F 19/3437* (2013.01); *G06T 2207/10072* (2013.01); *G06T 2207/20081* (2013.01); *G06T 2207/20124* (2013.01); *G06T 2207/30048* (2013.01)

(56) References Cited

U.S. PATENT DOCUMENTS

| | | | |
|---|---|---|---|
| 7,916,919 B2 | 3/2011 | Zheng et al. | |
| 8,098,918 B2 | 1/2012 | Zheng et al. | |
| 8,386,188 B2 | 2/2013 | Taylor et al. | |
| 2009/0105579 A1* | 4/2009 | Garibaldi | A61B 1/00158 600/409 |
| 2011/0201915 A1* | 8/2011 | Gogin | A61B 5/0456 600/407 |
| 2012/0022843 A1 | 1/2012 | Ionasec et al. | |
| 2012/0041301 A1 | 2/2012 | Redel | |
| 2012/0072190 A1 | 3/2012 | Sharma et al. | |
| 2012/0121151 A1 | 5/2012 | Bernhardt et al. | |
| 2012/0203530 A1 | 8/2012 | Sharma et al. | |

OTHER PUBLICATIONS

Peyrat et al., "A Computational Framework for the Statistical Analysis of Cardiac Diffusion Tensors: Application to a Small Database of Canine Hearts", IEEE TMI, 26(11): 1500-1514, 2007.

Mitchell et al., "A Two-Current Model for the Dynamics of Cardiac Membrane", Bulletin of Mathematical Biology, 65(5):767-793, 2003.

Powell, "Developments of NEWUOA for Minimization Without Derivatives", J. Num. Analysis, 2008.

Ten Tusscher, et al., "Cell Model for Efficient Simulation of Wave Propagation in Human Ventricular Tissue Under Normal and Pathological Conditions", Physics in Medicine and Biology, 51, pp. 6141-6156, 2006.

* cited by examiner

SYSTEM AND METHOD FOR PATIENT SPECIFIC PLANNING AND GUIDANCE OF ABLATIVE PROCEDURES FOR CARDIAC ARRHYTHMIAS

This application claims the benefit of U.S. Provisional Application No. 61/673,407, filed Jul. 19, 2012, the disclosure of which is herein incorporated by reference.

BACKGROUND OF THE INVENTION

The present invention relates to patient-specific planning and guidance of ablative procedures for cardiac arrhythmias using medical imaging data, and more particularly, to method and system for calculating advanced measurements to target ablation sites during an intervention.

Sudden cardiac death (SCD) is responsible for over 300,000 deaths per year in the United States. Severe cardiac arrhythmias, such as ventricular tachycardia (VT) or ventricular fibrillation (VF), are the most common causes of SCD. Currently, implantable cardioverter-defibrillator devices (ICD) are the primary treatment of choice for patients at high risk for VT or VF. These devices prevent life-threatening VT/VF events by automatically sending strong defibrillator shocks when VT/VF is detected. However, the morbidity associated with ICD shocks is high and ICDs do not provide complete protection against SCD. When arrhythmias become incessant or too severe, an alternative therapy becomes necessary.

Ablation procedures for cardiac arrhythmias have proven to be successful for a large variety of cardiac electrophysiology troubles. Atrial fibrillation (Afib), VT, or VF, for example, can be treated, or at least controlled, in several classes of patients. The general idea behind ablation therapy is to destroy the cells that trigger the arrhythmias. These cells can be ectopic, i.e., they trigger uncontrolled electrical signals spontaneously, or exits points slow conducting pathways that can be found, for example, around myocardium scars. The success of the ablation therapy relies on the ability of the electrophysiologist to identify the arrhythmogenic regions. While Afib ablation has become systematic in most patients, finding the regions to ablate in post myocardium infarction (MI) patients is extremely challenging due to the variability in scar geometry and local tissue substrate. Current practice is still lacking of a systematic clinical strategy, which may explain the rather unsatisfactory success rate of ablation therapies for VT (from 50% to 90%). There is therefore a need for efficient tools for improving ablative procedures as a primary therapy, in terms of maximizing outcomes, decreasing risks and minimizing intervention time.

BRIEF SUMMARY OF THE INVENTION

The present invention provides a method and system for patient-specific planning and guidance of ablative procedures for cardiac arrhythmias using medical imaging data. Embodiments of the present invention provide a technique for computing advanced measurements to better target ablation sites during an intervention. Embodiments of the present invention rely on a near real-time model of cardiac electrophysiology, and on inverse problem algorithms to calculate advanced measurements, such as, but not limited to, tissue substrate and depolarization/repolarization time maps, which can then be updated as additional data is acquired during the intervention. Furthermore, embodiments of the present invention can calculate cardiac electrophysiology under different virtual pacing, such that multiple pacing simulations can be tested in-silico. Combining the advanced measurements with the in-silico pacing simulations can guide electrophysiologists to the correct ablation sites while minimizing life-threatening risks for the patient.

In one embodiment of the present invention, a patient-specific anatomical heart model extracted from pre-operative cardiac image data is registered to a coordinate system of an intra-operative image acquired during an ablation procedure. One or more ablation site guidance maps are generated based on the registered patient-specific anatomical heart model and intra-operative patient-specific measurements acquired during the ablation procedure.

These and other advantages of the invention will be apparent to those of ordinary skill in the art by reference to the following detailed description and the accompanying drawings.

DETAILED DESCRIPTION

Figure 1:
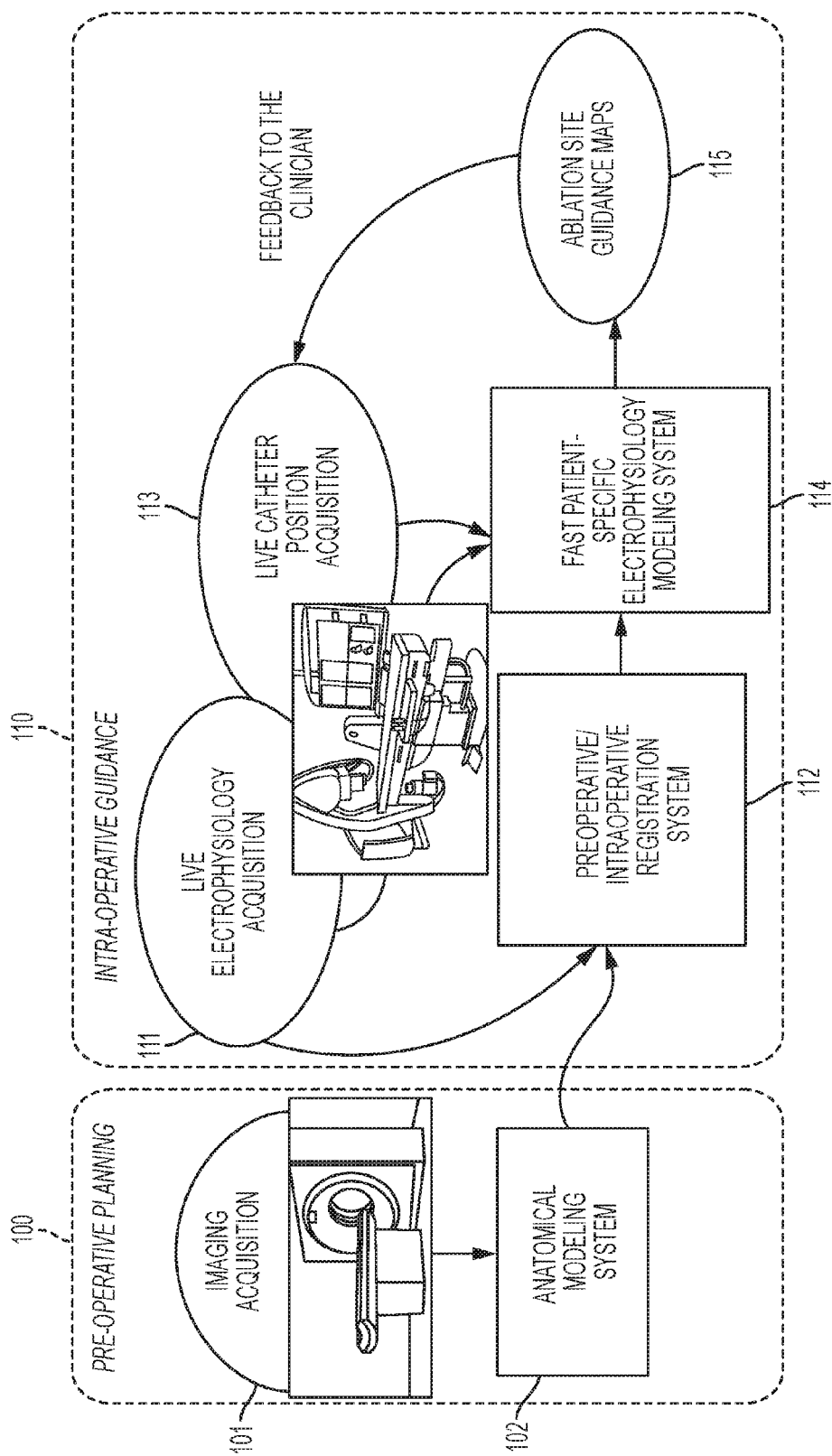
FIG. 1 illustrates a framework for patient-specific planning and guidance of ablative procedures for cardiac arrhythmias according to an embodiment of the present invention.

The present invention relates to patient-specific planning and guidance of ablative procedures for cardiac arrhythmias using medical imaging data. Embodiments of the present invention are described herein to give a visual understanding of the methods for patient-specific modeling and simulation using medical imaging data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

In post myocardium infarction (MI) patients, slow conducting zones around scars can make the electrical wave re-enter into regions behind the normal electrical front, which may eventually lead to VT. By ablating the exit points of these slow conducting regions, wave re-entries are prevented and VT treated. The current practice relies on a comprehensive, intra-operative electrophysiological study to identify the isthmuses and their exit points. A region of interest is first estimated from a comprehensive 12-lead electrocardiography (ECG) study. Endocardial mappings under sinus rhythm and different stimulation protocols are then performed to refine the region of interest. By measuring the potential amplitude on the endocardium under sinus rhythm, the electrophysiologist can identify the location of the scar and the slow conducting regions within a region of interest of >2 cm circumference. Since that region of interest is still too large to be ablated without significant consequences on the patient's heart condition, the identification of exit points is finally achieved by finding locations that induce VT through successive manual stimulation trial at pre-specified locations (e.g., right ventricle endocardium apex). The study of the 12-lead ECG combined with the measured potentials under pacing enables the electrophysiologist to identify the exit points that trigger VT. The procedure of localizing the ablation regions by inducing VT may be time consuming, and in many cases lasts more than 30 minutes, with a mortality of 2% mostly due to uncontrolled VT. Furthermore, during the procedure and ECG analysis, it may appear that epicardial ablation is necessary (10-30% of MI case, >30% of non MI cases), which further complicates the procedure.

Recently, advanced computational models of cardiac electrophysiology have been developed. These models are mainly targeted for hypothesis testing and cardiac physiology understanding. Several categories of models have been proposed, spanning from very detailed ionic models, which simulate the ionic interactions giving rise to the action potential, to phenomenological models, which simulate the transmembrane potential directly, to simplified Eikonal models. These models are commonly solved on generic cardiac anatomies using finite element or finite difference methods. Computational simulation of VT for VT pacing procedure and ablation therapy planning has been investigated, but such techniques are severely limited. An important limitation in existing computational simulation techniques art is the requirement of preoperative delayed enhanced magnetic resonance imaging (DE-MRI) data to map the scar anatomy in the model. However, patients at high risks of VT/VF already have an ICD in place, which prevents any MRI acquisition. Even in the case of MR-compatible ICD, the artifacts generated by the ICD electrodes in the MR images can be such that the identification of scar may be compromised. Moreover, acute VT patients usually do not receive a full MR study. Scar information must therefore be recovered during the intervention from endocardial mapping. Another limitation is the inherent computational complexity of the algorithms. Models are typically solved using finite elements, which can require hours to compute the electrical activity happening during one heart beat. These two limitations together currently prevent the use of computational models for preoperative planning and intra-operative guidance of therapies.

Embodiments of the present invention provide solutions to the above-mentioned issues by providing a fast system and method for calculating advanced electrophysiological measurements to better target ablation site during the intervention. Embodiments of the present invention rely on LBM-EP (Lattice-Boltzmann Method for Electrophysiology) technology, which provides a near real-time model of cardiac electrophysiology, and on inverse problem algorithms to calculate advanced measurements, such as tissue substrate and depolarization/repolarization time maps. These maps are updated as data is acquired during the intervention. Furthermore, since the system is generative, it can compute cardiac electrophysiology under different virtual pacing. As a result, several pacing stimulations can be tested in-silico. Combining the advanced measurements estimated by our system and the in-silico pacing protocol together can potentially guide electrophysiologists towards the region to ablate while minimizing life-threatening risks for the patient.

An advantageous feature of embodiments of the present invention is that a region targeted by an ablation procedure can be derived from a tissue diffusion map and an action potential duration (APD) map, which are calculated using an inverse problem algorithm based on intra-operative patient-measurements. In particular, these maps indicate slow conducting regions susceptible to trigger VT. Another advantageous feature of embodiments of the present invention is that the estimated maps and cardiac electrophysiology model parameters can be updated as data is acquired during the intervention to provide more accurate and targeted measurements. Another advantageous feature of embodiments of the present invention is that the refinement of the localization of candidate ablation sites can be achieved in silico by virtual myocardium pacing. This results in a prediction of the pacing locations that might trigger VT, which can then be confirmed in the patient.

Embodiments of the present invention provide a system and a method that can be used to assist electrophysiology interventions by providing the physician with clinically relevant values derived from a computational model of cardiac electrophysiology. This computational model reflects the actual patient conditions based on pre-operative and intra-operative patient data. Embodiments of the present invention utilize a fast computational model of the cardiac electrophysiology along with an automatic personalization method which relies on preoperative imaging data and intra-operative clinical data. Such a model and personalization approach allow embodiments of the present invention to effectively deal with the sparse nature of the intra-operative measurements. In addition, the derived clinical values can be updated in real-time by feeding the electrophysiological model with intra-operative data. More specifically, the computational model can be solved on a computational domain estimated automatically from pre-operative images of the heart (e.g. CT, US, three-dimensional rotational angiography, MRI) and can be coupled with an inverse problem algorithm to automatically estimate myocardium diffusion and action potential duration (APD) maps, which are updated intra-operatively as electrophysiological data (endocardial mapping, ECG leads, etc. under sinus rhythm or manual pacing) is acquired during an intervention. Using the advanced measurements estimated by the system, the physician performing the intervention can be guided towards the myocardium region to ablate. This information shall enable a gain in time during the identification phase of the ablation procedure, by reducing the number of manual measurements and pacing tests. Embodiments of the present invention also enable performing virtual VT pacing using the patient-specific data, prior to or during the intervention, to identify VT trigger points. This virtual pacing has the potential advantage of reducing the risk of triggering uncontrolled VT, which can be life-threatening for the patients (current mortality rate: 2%). Collectively, the method and system disclosed herein helps to improve the outcomes of therapeutic ablation procedures.

FIG. 1 illustrates a framework for patient-specific planning and guidance of ablative procedures for cardiac arrhythmias according to an embodiment of the present invention. As illustrated in FIG. 1, pre-operative planning 100 is performed prior to an ablation procedure (intervention) and intra-operative guidance 110 is performed during the intervention. In the pre-operative planning phase 100, imaging acquisition 101 is performed to acquire preoperative cardiac images and an anatomical modeling system 102 automatically estimates an anatomical model from preoperative cardiac images. Any imaging modality can be used at this stage, provided the heart is entirely visible (e.g. CT, rotational angiography, MRI, US, etc.). If no preoperative imaging data is available, generic, disease-specific anatomies can be employed. If the patient is suitable for MRI study, MRI imaging of myocardium scar can be performed to estimate the extent of the scar tissue and border zone (damaged but functional cells), and this information is then mapped onto the anatomical model. Similar information can be acquired from other imaging modalities, such as CT perfusion for example. In the intra-operative guidance phase 110, live electrophysiology acquisition 111 and liver catheter position acquisition 113 are performed, and a pre-operative/intra-operative registration system 112 registers the anatomical model into an intra-operative coordinate system. The registration is performed using positioning information provided by the angiography system and/or position fiducials provided by the electrophysiology system. The registered anatomical domain is given as input to a fast patient-specific electrophysiology modeling system 114. That fast patient-specific electrophysiology modeling system 114 also takes as input the live electrophysiological measurements (e.g., intracardial ECG) and the positions of the pacing catheters. Patient-specific cardiac electrophysiology is calculated given the intracardial ECG and the position of the pacing catheter. An inverse problem algorithm is used to compute ablation site guidance maps, including a tissue diffusion map and an action potential duration (APD) map that indicate slow conduction regions susceptible to trigger VT. To refine the localization of candidate ablation sites, the user can use the fast patient-specific electrophysiology modeling system 114 to perform virtual myocardium pacing to predict the pacing locations that would trigger VT, which can then be confirmed in the patient. As additional data is acquired during the intervention, the estimated ablation site guidance maps and model parameters of the patient-specific electrophysiology model are updated to provide more accurate and targeted measurements. It is to be understood that the anatomical modeling system 102, the pre-operative/intra-operative registration system 112, and the fast patient-specific electrophysiology modeling system 114 are implemented on one or more computer systems by a processor executing computer program instructions.

Figure 2:
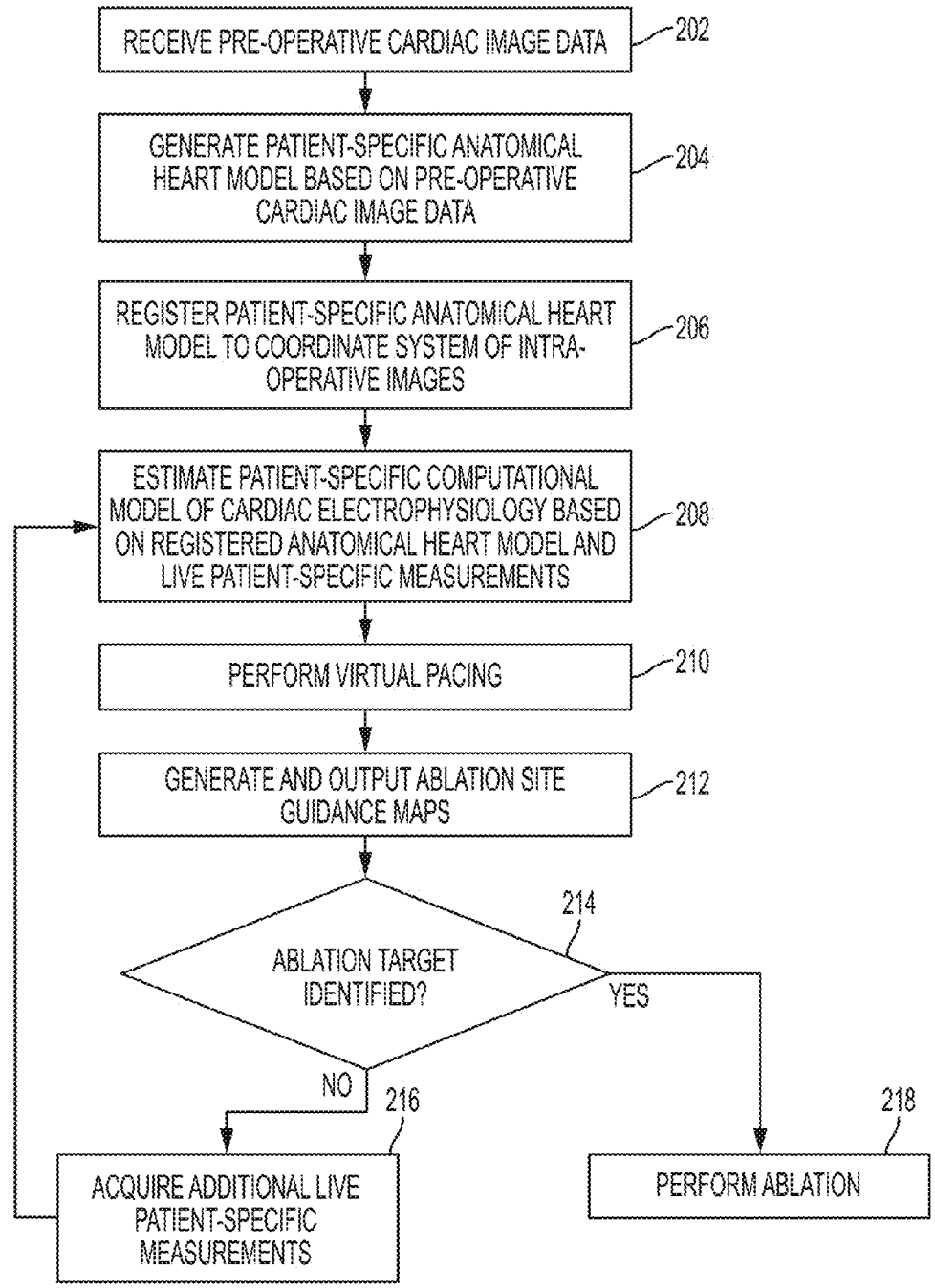
FIG. 2 illustrates a method of patient-specific planning and guidance of ablative procedures for cardiac arrhythmias according to an embodiment of the present invention.

FIG. 2 illustrates a method of patient-specific planning and guidance of ablative procedures for cardiac arrhythmias according to an embodiment of the present invention. The method of FIG. 2 transforms medical image data and electrophysiological measurements of a patient into ablation site guidance maps that can identify candidate locations for ablation and pacing locations that can trigger VT. At step 202, pre-operative cardiac image data of a patient is received. The pre-operative cardiac image data can be acquired using any type of medical imaging modality, such as computed tomography (CT), three-dimensional rotational angiography, magnetic resonance imaging (MRI), ultrasound (US), etc., provided that the heart is entirely visible in the medical image data. In an advantageous implementation, the pre-operative cardiac image data includes three dimensional (3D) medical image data. The pre-operative cardiac image data can be received directly from an image acquisition device, such as a CT scanner, a C-arm image-acquisition device, an MRI scanner, or an US scanner, or the pre-operative cardiac image data can be received by loading previously stored cardiac image data of the patient.

Figure 3:
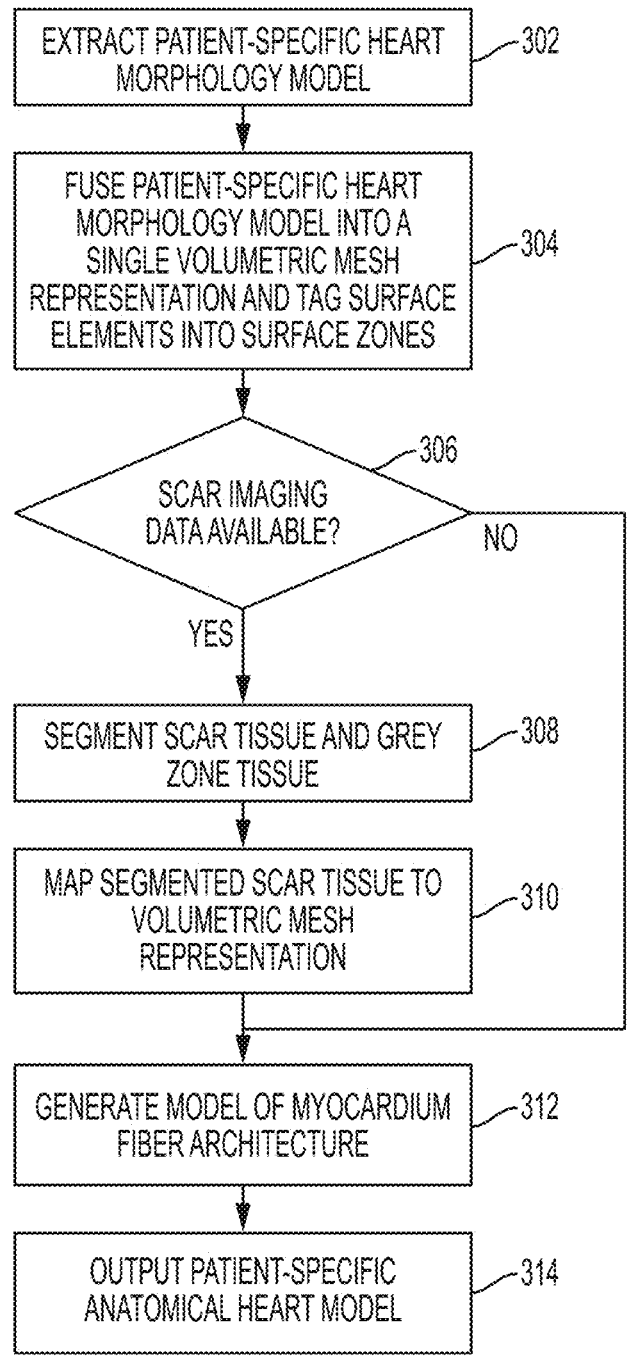
FIG. 3 illustrates a method for generating a patient-specific anatomical heart model according to an embodiment of the present invention.

At step 204, a patient-specific anatomical heart model is generated from the pre-operative image data of the patient. According to a possible implementation, this step can be performed in a pre-operative planning stage and the resulting patient-specific anatomical model can be stored in a memory or storage of a computer system until the time of the patient's intervention. Alternatively, this step can be performed at the beginning of or immediately prior to the patient's intervention. FIG. 3 illustrates a method for generating a patient-specific anatomical heart model according to an embodiment of the present invention. The method of FIG. 3 transforms pre-operative cardiac image data to generate a patient-specific anatomical model of the patient's heart. The method of FIG. 3 can be used to implement step 204 of FIG. 2.

Referring to FIG. 3, at step 302, a patient-specific heart morphology model is extracted from the pre-operative cardiac image data. The patient-specific heart morphology model can be a comprehensive geometrical model that represents the patient-specific heart morphology. In an advantageous embodiment, the patient-specific heart morphology model includes individual anatomical models representing the morphology of various heart components. The models are highly modular and can be customized depending on the application. The complete heart model can comprise the left ventricle (LV), left atrium (LA), left outflow tract, aortic root, pulmonary veins, right ventricle (RV), right atrium (RA), right outflow tract, RV neck, and veins. Papillaries and trabeculae can also be obtained, from CT images for instance. Each of these components can be used individually or jointly according to data availability and clinical application. In an advantageous embodiment, for VT/VF ablation therapy, the LV and RV anatomical models estimated from the pre-operative cardiac image data are used. In a possible implementation, only the LV and RV are explicitly modeled. In another possible implementation, models for all of the heart chambers are extracted. It is also possible that the comprehensive model including all of the heart components is extracted. The modularity of this framework enables using images in which only part of the anatomy is visible. For example, pre-operative US images can be used to extract the LV model, but the present invention is not limited thereto.

The anatomical model for each heart component can be extracted individually. In particular, for each heart chamber, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. Each classifier can be a probabilistic boosting tree (PBT) classifier trained based on annotated training data. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

At step 304, the patient-specific heart morphology model is fused into a single volumetric mesh representation and surface elements of the mesh are tagged into surface zones. For example, in the case of VT/VF ablation therapy, the patient-specific LV and RV anatomical models can be fused into a single anatomical model of the bi-ventricular myocardium. In particular, the LV and RV anatomies extracted in step 402 are fused into a single volumetric mesh representation. The LV and RV models can be fused into a single volumetric mesh representation, on which vertices are tagged into surface zones (LV endocardium, LV septum, RV endocardium, RV septum) according to the underlying anatomy of the estimated surface models. According to an advantageous embodiment, tetrahedral elements can be used to accurately represent the details of the bi-ventricular anatomy.

At step 306, it is determined if scar imaging data is available in the pre-operative cardiac imaging data. Certain types of medical imaging modalities, such as DE-MRI or CT perfusion, can be used to accurately localize scar tissue in a patient's heart. However, these types of medical image data may not be available for all patients. For example, because VT patient's typically wear implantable cardioverter-defibrillator (ICD) devices already, a pre-operative MRI often cannot be performed to quantify the extent of the scar tissue. Even in the case of MRI-compatible ICD devices, the artifacts generated by the ICD electrodes in MRI images can compromise identification of the scar tissue. If it is determined that scar imaging data is available for the patient, the method proceeds to step 308. If it is determined that scar imaging data is not available for the patient, the method proceeds to step 312.

At step 308, if the scar imaging data is available in the pre-operative cardiac imaging data, the scar tissue and grey zone tissue are segmented in the pre-operative cardiac imaging data. The grey zone tissue is a border zone surrounding the scar tissue. In an advantageous implementation, the scar tissue and border zone surrounding the scar tissue can be segmented by detecting myocardial borders of the heart in a sequence image data (e.g., cine DE-MRI data) taken over multiple cardiac phases, and then classifying the detected myocardial borders as viable tissue or non-viable tissue (i.e., scar tissue) using a trained support vector machine (SVM), or other supervised learning technique. Such a method for segmenting scar tissue is DE-MRI image data is described in greater detail in U.S. Pat. No. 7,668,354, which is incorporated herein by reference.

At step 310, the segmented scar tissue and surrounding border zone is mapped to the volumetric mesh representation generated at step 304. For example, the tetrahedra shape of the volumetric mesh representation of the fused LV and LA can be locally modified to match the boundaries of the segmented scar tissue and border zone.

At step 312, a model of myocardium fiber architecture is generated based on the patient's heart geometry. In one embodiment, in-vivo diffusion tensor (DT) MR images of the patient's cardiac fibers are directly mapped to the anatomical model through image registration. In this case, the DT MR image is non-linearly registered to the medical image in which the LV and RV models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors Application to a Small Database of Canine Hearts", IEEE TMI, 26(11):1500-1514, 2007, which is incorporated herein by reference, is used to reorient the tensors once the tensors are registered to the anatomical model. It is also possible, that an atlas of fiber architecture is available and the atlas is registered to the patient-specific anatomical model suing standard image registration techniques.

In another embodiment, if in-vivo DT MRI is not available, the model of fiber orientation may be computed directly from the anatomical model using a rule-based method. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, from $-70$ on the epicardium to $+70$ on the endocardium (values that can be defined by the user). Similarly, the sheet direction, which is defined by the angle $\beta$ with respect to the outward transmural axis, varies transmurally from $+45$ on the epicardium to $-45$ on the endocardium (values that can be defined by the user). $\alpha$ and $\beta$ are computed for each point of the volumetric bi-ventricular myocardium mesh between the apex and basal plane based on the geodesic distance to the endocardia and epicardia identified by the facet tags: $\alpha=(d_{epi}\alpha_{endo}+d_{endo}\alpha_{epi})/(d_{endo}+d_{epi})$, where $d_{epi}$, $d_{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. For orthonormality preservation, the interpolation can be performed using a Log-Euclidean framework.

Figure 4:
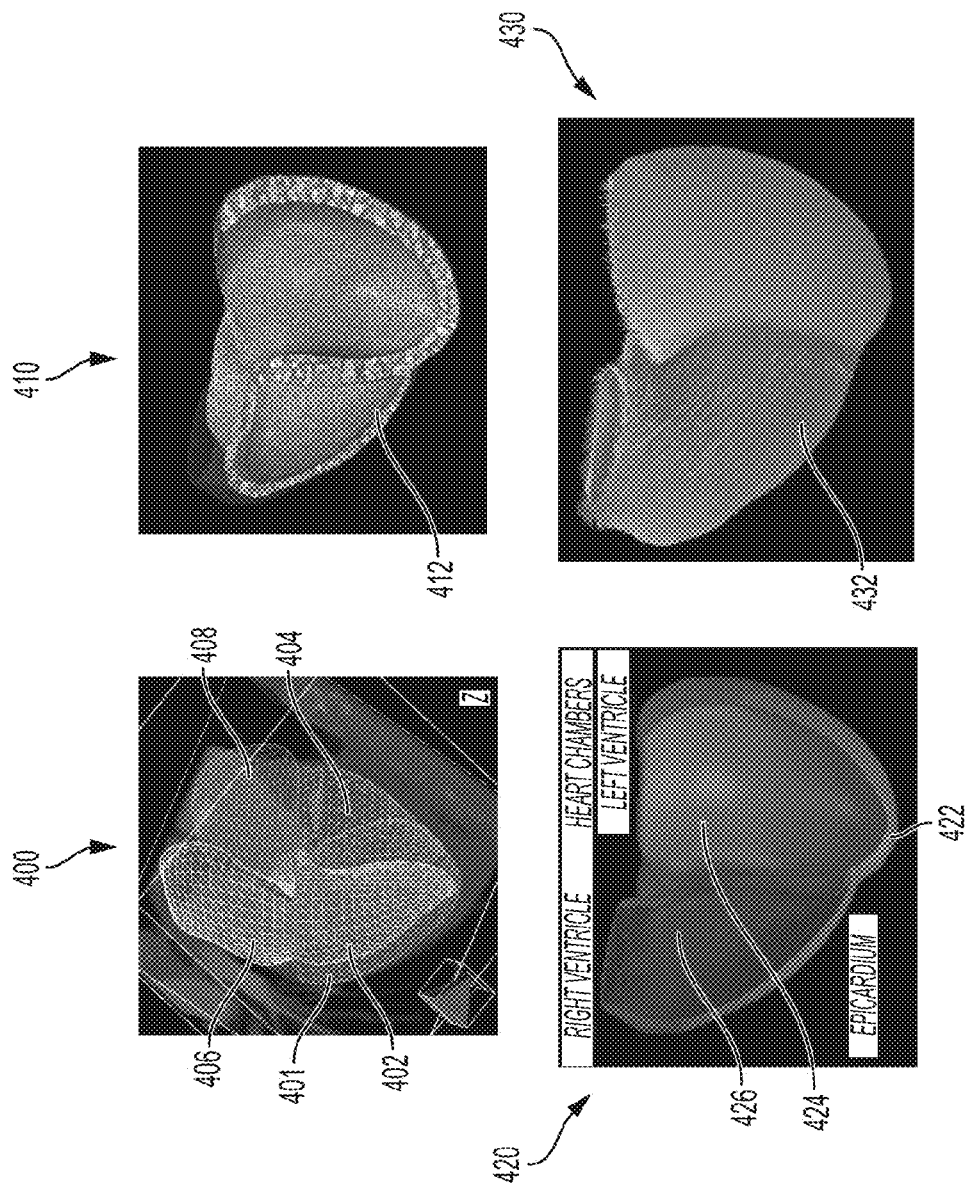
FIG. 4 illustrates exemplary results for extracting a patient-specific anatomical model.

At step 314, the patient-specific anatomical model is output. The patient-specific anatomical model generated in steps 302-312 is a patient-specific volumetric mesh representation of at least a portion of the heart (e.g., the bi-ventricular myocardium) that includes segmented scar tissue of the patient, if available, and a patient-specific model of ventricular myocardium fiber architecture. The patient-specific anatomical model can be output by displaying the patient-specific anatomical, for example, on a display device of a computer system. The patient-specific anatomical model can also be output by storing the patient-specific anatomical model on a memory or storage of a computer system. FIG. 4 illustrates exemplary results for extracting a patient-specific anatomical model. As illustrated in FIG. 4, image 400 shows patient-specific anatomical models of the left ventricle epicardium 401, left ventricle endocardium 402, right ventricle 404, left atrium 406, and right atrium 408, automatically extracted from 3D CT image data. Image 410 shows a fused volumetric anatomical mesh 412 resulting from fusing the left ventricle epicardium, left ventricle endocardium, and right ventricle anatomical models. Image 420 shows exemplary results of automatic mesh tagging of the volumetric mesh. In particular, surface elements of the volumetric mesh in image 420 are tagged into surface zones of epicardium 422, left ventricle 424, and right ventricle 426. Image 430 shows exemplary results of generating the patient-specific model of the ventricular myocardium fiber architecture 432.

Returning to FIG. 2, at step 206, the patient-specific anatomical heart model is registered to a coordinate system of intra-operative images acquired during an ablation procedure. Interventions, such as ablation procedures, are typically guided by a sequence of 2D fluoroscopic images which are acquired in real-time during the intervention. The patient-specific anatomical heart model extracted from the pre-operative cardiac image data is registered to the coordinate system of the 3D fluoroscopic images. In one possible implementation, the patient-specific anatomical model can be manually registered into the angiography space (i.e., the coordinate system of the fluoroscopic images). For example, this registration can be performed manually by a physician using bi-plane fluoroscopic image acquisition (90 degrees between detectors) and a contrast medium injected into the patient to allow the physician to visualize the anatomy in the fluoroscopic images.

In another possible implementation, an intra-operative three-dimensional rotational angiography image of the patient's heart can be acquired using a C-arm image acquisition device. A C-arm image acquisition device rotates around a patient to acquire fluoroscopic images at different projection angles and reconstructs a 3D rotational angiography image from the set of 2D projections. Since the C-arm image acquisition device is also used to acquire the intra-operative fluoroscopic images used to guide the ablation procedure, the coordinate system of the 3D rotational angiography image is the same as the coordinate system of the intra-operative fluoroscopic images. In this case, a method for multi-modal model-based fusion is used to register the pre-operative anatomical model to the 3D rotational angiography image. In particular, a probability map of cardiac pericardium is computed from the rotational angiography image using a machine-learning algorithm, such as Marginal Space Learning (MSL). Additional details regarding MSL-based segmentation are described in U.S. Pat. No. 7,916,919, which is incorporated herein by reference. The preoperative surface mesh of patient's pericardium is then mapped to the rotational angiography coordinate system using an optimization algorithm that maximizes the integrated probability along the surface mesh. The resulting deformation is extrapolated to the volume domain by thin-plate spline interpolation. Finally, the preoperative volumetric model is registered by applying the dense deformation field. Myocardium fibers are reoriented accordingly by using the local Jacobian matrix of the deformation field.

In another possible implementation, if no intra-operative 3D imaging data is available, the volumetric anatomical model can be rigidly registered onto the intra-operative coordinate system using spatial fiducials provided by the tracking capabilities of an electrophysiological mapping system. Endocardial mapping systems often provide 3D markers of key anatomical landmarks, such as the aortic valve, LV apex, etc. These landmarks are used to compute a 3D rigid transformation using the iterative closest point (ICP) method to register the volumetric model to the intra-operative coordinate system.

In a situation in which no 3D rotational angiography data is available and no endocardial mapping fiducials are available for registering the pre-operative patient-specific anatomical model to the intra-operative coordinate system, external fiducials may be placed on the patient's chest during pre-operative and intra-operative image acquisitions. These fiducials can then be employed to calculate a rigid transformation to register the patient-specific anatomical model to the intra-operative image data. It is also possible that catheter fiducials may be available in the fluoroscopy images for pre-preoperative/intra-operative anatomical model registration.

When possible, the left atrium is used as a surrogate to drive the registration methods described in the previous points. This is achieved as follows: 1) a detailed left heart model including the LV and LA is estimated on the preoperative images; 2) the LA is then registered to the angiography space with any of the above mentioned implementations; 3) the LV "follows" the LA transformation as the two structures are anatomically attached to each other. That is, the transformation used to register the LA in the pre-operative anatomical model with the LA in the intra-operative coordinate system is then applied to register the entire patient-specific anatomical model. Since the system and method described herein are modular, any pre-operative/intra-operative registration method can be utilized. It is also possible that a coupled imaging system, such as an X-ray/MRI set-up, can be employed to perform this registration. Further, any of the above described techniques can be utilized individually or jointly for improved accuracy. Although, the intra-operative images are described herein as fluoroscopic images, the present invention is not limited thereto. For example, embodiments of the present invention can similarly be applied to cardiac ablation therapy under MRI or ultrasound guidance, as well.

Figure 5:
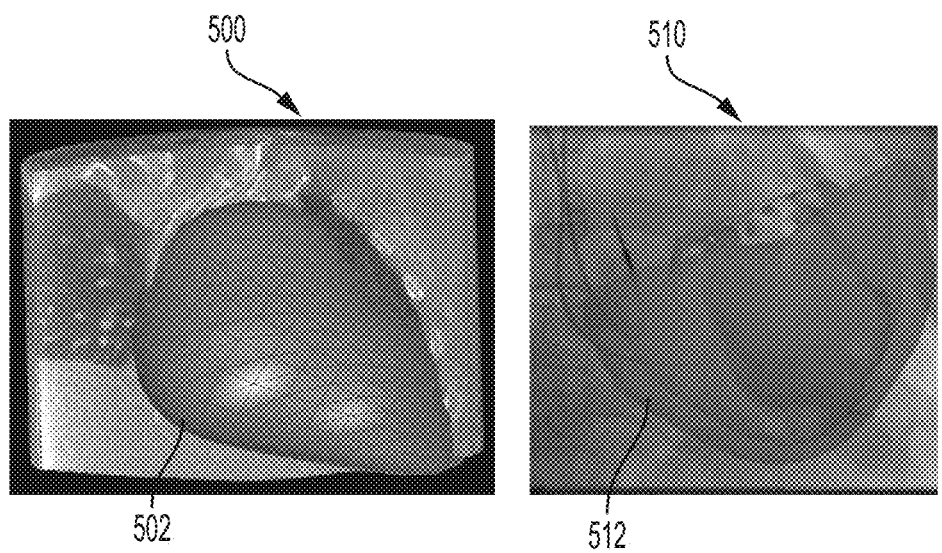
FIG. 5 illustrates exemplary results of registering a pre-operative patient-specific anatomical model to a coordinate system of intra-operative images.

FIG. 5 illustrates exemplary results of registering a pre-operative patient-specific anatomical model to a coordinate system of intra-operative images. Image 500 of FIG. 5 shows a pre-operative patient-specific anatomical heart model 502 registered to a 3D intra-operative rotational angiography image. Image 510 if FIG. 5 shows a pre-operative patient-specific anatomical heart model 512 overlaid on an intra-operative 2D fluoroscopic image.

Returning to FIG. 2, at step 208, a patient-specific computational model of cardiac electrophysiology is estimated based on the registered anatomical heart model and live patient-specific measurements acquired during the intervention. The patient-specific computational model of cardiac electrophysiology, once fit based on the patient-specific measurements acquired during the intervention, is used to generate estimated ablation site guidance maps (ASGM), which are maps of advanced measurement estimates over various locations in the heart. In an advantageous embodiment of the present invention, due to the sparse nature of intra-operative measurements, a cardiac electrophysiology model is used to reconstruct the ASGM over the domain of the patient-specific anatomical heart model. Examples of ASGM are tissue diffusivity maps, action potential duration maps, dynamic maps of cardiac potentials, depolarization time maps, and repolarization time maps. The process of estimating the AGSM for the patient can also be seen as fitting the cardiac electrophysiology model to the patient-specific measurements acquired during the intervention. The patient-specific measurements can include electrocardiograph (ECG) measurements (e.g., standard, 12 lead, etc.), an endocardial mapping, and a current position of a pacing catheter.

Figure 6:
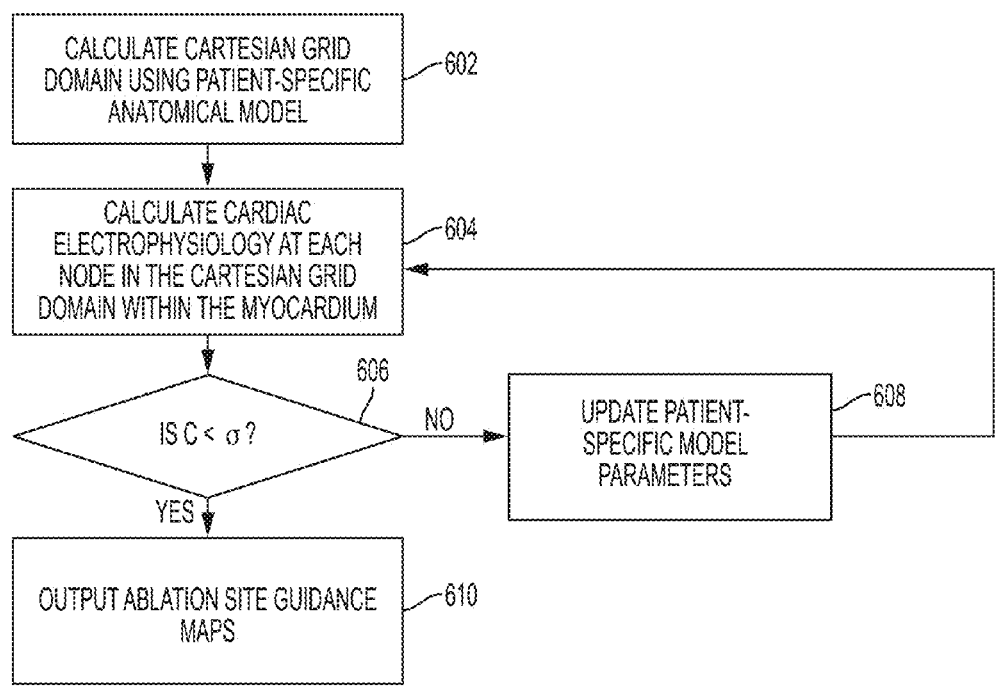
FIG. 6 illustrates a method for estimating a patient-specific computational model of cardiac electrophysiology and generating ablation site guidance maps (ASGM) for a patient according to an embodiment of the present invention.

FIG. 6 illustrates a method for estimating a patient-specific computational model of cardiac electrophysiology and generating ablation site guidance maps (ASGM) for a patient according to an embodiment of the present invention. The method of FIG. 6 transforms a patient-specific anatomical heart model and patient-specific measurements acquired during an intervention into estimated ASGM by fitting a cardiac electrophysiology model to the patient-specific measurements based on the patient-specific anatomical heart model. The method of FIG. 6 can be used to implement step 208 of FIG. 2.

Figure 7:
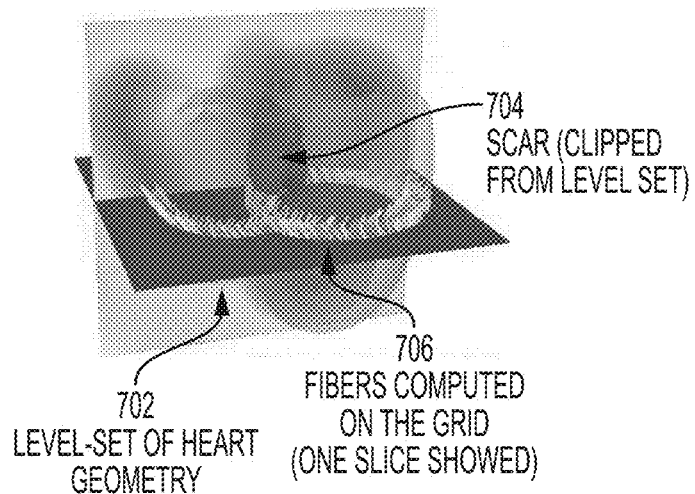
FIG. 7 illustrates an exemplary Cartesian grid domain for cardiac electrophysiology computation.

Referring to FIG. 6, at step 602, a Cartesian grid domain for electrophysiology computations is calculated using the registered patient-specific anatomical heart model. A Cartesian grid, possibly with unequal and spatially varying spacing, is first generated in a bounding box surrounding the anatomical model. Grid spacing can be defined by the user or fixed in the system. A level-set representation is then calculated from the patient-specific anatomical mesh as follows. For every node x of the grid, the shortest distance to the anatomical model mesh is calculated, and assigned to that node. In an advantageous embodiment, nodes inside the myocardium are defined by positive distances, and nodes not inside the myocardium are defined by negative distances. The opposite convention can be utilized as well without any modification. Nodes at myocardium, endocardia, and epicardium are tagged as such, as well as septal nodes. Available scars and border zones are also reported in the domain through additional level-set information. Fiber orientation f(x) are mapped to each node using rasterization techniques or recomputed from the mapped endocardial and epicardial zones. A diffusion coefficient D(x) and an action potential duration APD(x) is assigned to every myocardial node x of the Cartesian grid. Cell model parameters can also be mapped spatially at each node. FIG. 7 illustrates an exemplary Cartesian grid domain for cardiac electrophysiology computation. As shown in FIG. 7, the domain is represented using a signed level-set representation 702 of the registered anatomical model. Available scar information is clipped from the level-set representation 702 of the registered anatomical model and mapped as an additional level-set 704. Fiber orientation 706 (shown on one slice) is specified at each node of the domain.

Returning to FIG. 6, at step 604, cardiac electrophysiology is calculated at each node of the Cartesian grid domain within the myocardium. According to an advantageous embodiment of the present invention, cardiac electrophysiology is calculated at each node within the myocardium using the Lattice-Boltzmann Method for Electrophysiology (LBM-EP) to solve a cardiac electrophysiology model at each node. The cardiac electrophysiology model calculates the variation of the transmembrane potential v(x,t) over time according to the mono-domain equation:

$$\frac{dv(x,t)}{dt} = R(x,t) + \nabla \cdot D(x)K(x)\nabla v(x,t), \quad (1)$$

where R(x,t) is a reaction term describing the cellular mechanisms giving rise to the action potential, D(x) is the local diffusivity to be estimated from the patient-specific data, K(x) is the anisotropy matrix defined by $(1-\rho)f(x)f(x)^T + \rho\mathrm{Id}$, $\rho$ being the ratio between the cross-fiber diffusivity and the fiber diffusivity (typically $\rho=0.11-0.25$). It is also possible to use orthotropic or fully anisotropic tensors K(x) for improved characterization of the fiber architecture.

The choice of the reaction term R(x,t) depends on the cellular model of cardiac electrophysiology that is used. The method disclosed herein is modular in that it can handle any standard mono-domain models, such as, but not limited to the "Mitchell-Schaffer model" proposed in Mitchell et al., "A Two-Current Model for the Dynamics of Cardiac Membrane", *Bulletin of Mathematical Biology*, 65(5):767-793, 2003, or the model proposed in Ten Tusscher, et al., "Cell Model for Efficient Simulation of Wave Propagation in Human Ventricular Tissue Under Normal and Pathological Conditions", *Physics in Medicine and Biology*, 51, pp 6141, 2006. For the Mitchell-Schaeffer model for instance, we have:

$$R(x,t) = \frac{h(x,t)v^2(x,t)(1-v(x,t))}{\tau_{in}} - \frac{v(x,t)}{\tau_{out}} + J_{stim}(x). \quad (2)$$

In this equation $J_{stim}(x)$ is an external stimulus current. When the electrophysiologist is pacing the heart at a given location during the intervention, the position of the pacing catheter is tracked using an embedded tracking method (e.g., electromagnetic tracking, bi-plane image-based tracking, etc.), and the position of the pacing catheter returned by the embedded tracking method is used to add a stimulus current to the model through $J_{stim}(x)$ at the acquired position. Virtual pacing is achieved by adding $J_{stim}(x)$ at a spatial location chosen by the user or chosen automatically by the system. The amount of current that is added to the model is obtained from the catheter manufacturer specifications.

In Equation (2), h(x,t) is a gating variable that controls the state of the ion channels according to the following ordinary differential equation:

$$\frac{dh(x,t)}{dt} = \begin{cases} \frac{1-h(x,t)}{\tau_{open}} & \text{if } v(x,t) < v_{gate} \\ \frac{-h(x,t)}{\tau_{close}} & \text{otherwise.} \end{cases}$$

Figure 8:
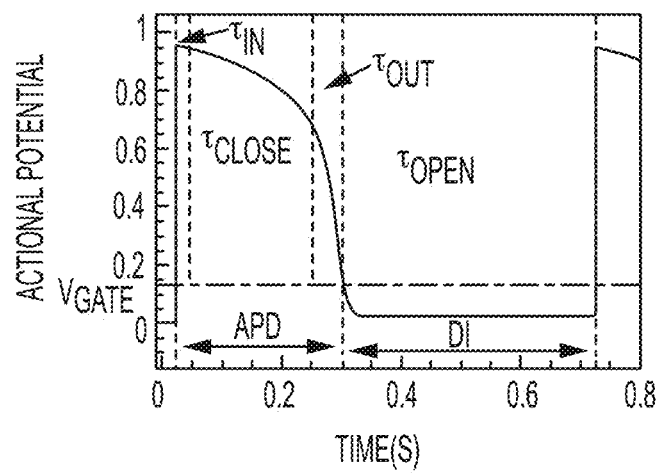
FIG. 8 illustrates relationships between model parameters and the shape of the action potential for the Mitchell-Schaeffer cardiac electrophysiology model.

$v_{gate}$ is a potential threshold, and $T_{in}$, $T_{out}$, $T_{open}$ and $T_{close}$ are parameters controlling the shape of the action potential. FIG. 8 illustrates relationships between model parameters and the shape of the action potential for the Mitchell-Schaeffer model. As shown in FIG. 8, the maximum action potential duration APD(x) is directly related to $T_{close}(x)$ according to the formula $APD_{max}(x) = T_{close}(x)\ln(T_{out}/(4T_{in}))$. In an advantageous embodiment of the present invention, only D(x) and $T_{close}(x)$ are estimated, the other parameters are kept constant to their default (i.e. nominal) values. However, it is also possible to implement this method to estimate these additional parameters as well.

Equation (1) is solved using the Lattice-Boltzmann method, referred to herein as LBM-EP. LBM-EP is a highly parallelizable algorithm to solve mono-domain electrophysiology equations. The LBM-EP algorithm is described in greater detail in U.S. patent application Ser. No. 13/780,230, filed on Feb. 28, 2013 and entitled "Method and System for Fast Patient-Specific Cardiac Electrophysiology Simulations for Therapy Planning and Guidance", which is incorporated herein by reference in its entirety. Contrary to standard finite-element methods, LBM-EP does not explicitly solve the reaction-diffusion equation but rather computes the "movement" of particles on a Cartesian grid, from which the reaction-diffusion behavior emerges. The particles can move according to fixed directions (or connectivities), with a certain probability. The algorithm includes two node-wise steps: streaming, which makes the particle jump from one node to another; and collision, which takes care of mass preservation and boundary conditions. It can be mathematically shown that this simple algorithm reproduces dynamics of the reaction-diffusion equation. In the method of FIG. 6, domain boundaries are represented as level-sets and tissue anisotropy is modeled. Since the method is node-wise, the algorithm is highly parallelizable. In an advantageous embodiment, the method can be implemented on a graphics processing unit (GPU), which enables near real-time and accurate cardiac electrophysiology computation during an intervention, such as an ablation procedure. In sinus rhythm, the electrocardiography model is computed with periodic stimulus at the septum to mimic the effects of the His bundle. The electrocardiography model can be initialized with high diffusivity coefficients on the endocardia to mimic the effect of Purkinje fibers, and lower diffusivity throughout the myocardium. These initial values are then updated in one or more subsequent iterations based on the patient-specific measurements received during the intervention to fit the cardiac electrocardiography model to the patient-specific measurements. It should be noted that since the framework relies on Cartesian grids, it is relatively simple to add more structural information in the model. For instance, Purkinje fibers, if available, can be added directly into the domain through rasterization. The His bundle and other electrophysiology bundles can be integrated similarly.

A set of ablation site guidance maps are generated based on the cardiac electrocardiography calculated at each node in the myocardium in step 604. In particular, in an advantageous implementation, the outputs of step 604 are 0 a time varying 3D potential map; ii) a 3D map of depolarization times $t_{dep}(x) | v(x, t_{dep}-dt) < v_{gate}, v(x, t_{dep}) > v_{gate}$; and iii) a 3D map of repolarization times $t_{rep}(x) | v(x, t_{dep}-dt) > v_{gate}, v(x, t_{dep}) < v_{gate}$. Additionally, other ablations site guidance maps, such as a 3D map of tissue diffusivity D(x) and a 3D map of action potential duration APD(x), can also be generated in step 604.

At step 606, it is determined if a cost function C based on the calculated depolarization times $t_{dep}(x)$ and repolarization times $t_{rep}(x)$ is less than a threshold σ. In particular, after having calculated the depolarization times $t_{dep}(x)$ and repolarization times $t_{rep}(x)$ for each node in the myocardium, these values are compared with current intra-operative endocardial mapping measurements and ECG measurements for the patient. In an advantageous implementation, the cost function C can be expressed as:

$$C = L_1 f_1(t_{dep}(x), t_{measured\ dep}(x)) + L_2 f_2(t_{rep}(x), t_{measured\ rep}(x)) + L_3 f_3(ECG_{sim}, ECG_{measured}), \quad (3)$$

where $t_{measured\ dep}(x)$ and $t_{measured\ rep}(x)$ are the depolarization and repolarization times determined from the current intra-operative endocardial mapping measurements, $ECG_{sim}$ refers to ECG features resulting from the simulation performed in step 604 to calculate the cardiac electrophysiology, $ECG_{measured}$ refers to the measured ECG features in the current intra-operative ECG measurements, $L_1$, $L_2$, and $L_3$ are weighting parameters, and $f_1$, $f_2$, and $f_3$ are respective distance functions for determining a distance between the two input variables. Examples of distance functions include the L2 or L1 norm, normalized cross-correlation, mutual information, etc.

If the cost function C in Equation 3 is greater than the threshold a, the method proceeds step 608. If the cost function C in Equation 3 is less than the threshold a, the method proceeds step 610.

At step 608, when the cost function C is greater than the threshold a, the patient-specific model parameters of the cardiac electrophysiology model are updated based on the intra-operative patient-specific measurements. In particular, an inverse problem algorithm is utilized to automatically estimate the diffusivity D(x) and action potential duration APD(x) parameters of the cardiac electrophysiology model based on the current intra-operative endocardial mapping measurements and ECG measurements for the patient. The aim of the inverse problem algorithm is to determine D(x) and APD(x) that minimize the cost function C of Equation 3. Examples of well known inverse problem algorithms that can be used to implement this minimization include trust regions, Kalman filtering, and variational approaches. To make the computation more efficient, D(x) and APD(x) can be defined zone-wise, with finer, smaller regions around a region of interest for ablation identified through the 12-lead ECG analysis. A multi-level, hierarchical approach can also be utilized.

As more patients are processed using this method, the range of parameters can be analyzed to provide better estimates for subsequent estimations (new patients, different pacing, etc.). Furthermore, a statistical model of the space of parameters D(x) and APD(x) with respect to heart geometry, scar extent, and stimulation protocol can be learned to further constrain the search space for future patients. Accordingly, once such a statistical model is learned, initial estimates for D(x) and APD(x) can be determined using the learned statistical model.

Once the patient-specific parameters D(x) and APD(x) of the cardiac electrophysiology model are updated, the method returns to step 604 and re-calculates the cardiac electrophysiology for each node within the myocardium using the updated model parameters. The method repeats steps 608, 604, and 606 until the cost function C is less than the threshold σ, indicating that the cardiac electrophysiology model is sufficiently fit to the current patient-specific intra-operative measurements. This results in the patient-specific computational model of cardiac electrophysiology for the patient.

At step 610, when the cost function C is less than the threshold a, the ablation site guidance maps (ASGM) are output. In particular, the ASGM are displayed on a display device in real-time or near real-time during the intervention. The ASGM can include a time varying 3D potential map, a 3D map of depolarization times, a 3D map of repolarization times, a 3D map of tissue diffusivity, and 3D map of action potential duration. These maps can be used to identify slow conducting regions and exit points to be ablated. In particular, a region to target by the ablation procedure can be derived from the tissue diffusivity map and the action potential duration map, which indicate slow conducting regions susceptible to trigger VT. Similarly, dynamic maps of action potentials or depolarization isochrones can be displayed to illustrate simulated VT when virtual pacing is performed. The maps can be displayed simultaneously, sequentially, or selectively, to the electrophysiologist to guide him or her during the intervention.

Returning to FIG. 2, at step 210, virtual pacing is performed using the patient-specific computational model of cardiac electrophysiology. Once the cardiac electrophysiology model is fit to the current intra-operative patient-specific parameters, this patient-specific computational model of cardiac electrophysiology is generative, and can be used to perform virtual pacing to investigate VT trigger points without actual testing on the patient. In particular, the patient-specific computational model of cardiac electrophysiology can simulate the cardiac electrophysiology of the patient in response a virtual pacing stimulus being applied at various locations in the computational domain. In a possible implementation, since the system is generative, the user (e.g., physician) can select locations to virtually pace the heart, given the current estimate of the diffusivity map D(x) and the action potential duration map APD(x). The user can input a spatial location for a virtual pacing catheter, for example using an input device, such as a mouse, touch screen, etc., of a computer system to select a spatial location on one of the displayed ablation site guidance maps. A stimulus current $J_{stim}(x)$ is added at that point at user-defined frequencies, and the cardiac electrophysiology model is solved to calculate the cardiac electrophysiology at each node in the myocardium over a simulated time period, as described above in step 604 of FIG. 6. Stimulation points that triggered VT in the model can then be used to guide the electrophysiologist towards the region to ablate. In an alternative implementation, systematic virtual pacing may be automatically applied by rasterizing the model, in order to detect potential regions to ablate. In particular, a sampling scheme can be used to automatically select virtual pacing locations at which to apply the stimulus current, and for each of the virtual pacing locations, the cardiac electrophysiology for each node is automatically calculated over a simulated time period using the patient-specific computational model of cardiac electrophysiology with a stimulus added at that virtual pacing location at a plurality of different frequencies. Virtual pacing locations that result simulated VT can be stored as VT trigger point candidates. This allows the user to detect trigger points that can cause VT quickly and without actual testing on the patient.

At step 212, ablation site guidance maps (ASGM) are generated based on the patient-specific computational model of cardiac electrophysiology and the virtual pacing, and the ASGM are output. Dynamic maps of action potentials or depolarization isochrones can be displayed to illustrate simulated VT in response to the stimulus current when the virtual pacing is performed. Furthermore, a map of VT trigger point candidates, for which the virtual pacing resulted in simulated VT can be generated and displayed to the user on a display device. The ASGM can also include a time varying 3D potential map, a 3D map of depolarization times, a 3D map of repolarization times, a 3D map of tissue diffusivity, and 3D map of action potential duration. The 3D potential map can be generated based on the simulated potential variations calculated using the patient-specific computational model of cardiac electrophysiology, and the 3D maps of depolarization and repolarization times can be generated based on the 3D potential map. The 3D map of tissue diffusivity and the 3D map of action potential can be generated by mapping the fitted tissue diffusivity and action potential duration parameters of the patient-specific computational model of cardiac electrophysiology over the nodes of the spatial domain. These maps can be used to identify slow conducting regions and exit points to be ablated. In particular, a region to target by the ablation procedure can be derived from the tissue diffusivity map and the action potential duration map, which indicate slow conducting regions susceptible to trigger VT, and the map of VT trigger point candidates resulting from the virtual pacing. The maps can be displayed simultaneously, sequentially, or selectively, to the electrophysiologist to guide him or her during the ablation procedure.

Although in the embodiment of FIG. 2, the ablation site guidance maps are generated after the virtual pacing is performed, the present invention is not limited thereto. The virtual pacing may be an optional step of the panning and guidance method, that could be performed at the discretion to the physician performing the ablation procedure or not at all. For example, in some embodiments of the present invention, once the patient-specific computational model of cardiac electrophysiology is estimated, the ablation site guidance maps (ASGM) can be generated using the patient-specific computational model of cardiac electrophysiology without any virtual pacing. Further, in some embodiments of the present invention, ablation site guidance maps (ASGM) can be generated using the patient-specific computational model of cardiac electrophysiology prior to virtual pacing, with additional maps being generated based on the virtual pacing.

At step 214, it is determined if an ablation target has been identified based on the ablation site guidance maps. If an ablation target has not been identified, the method proceeds to step 216. If an ablation target has been identified, the method proceeds to step 218.

At step 216, additional live patient-specific measurements are acquired during the ablation procedure. The electrophysiologist can also use the ablation site guidance maps, resulting from steps 208-212 to identify myocardium regions to investigate more deeply. The regions can be regions that need additional measurements to achieve finer ablation site targeting. The additional measurements can include additional endocaridal mappings and additional ECG measurements, and can be used to improve the accuracy of estimated measurements and the predicted stimulation points in those regions. Once the additional live patient-specific measurements are acquired at step 216, the method returns to step 208, and the patient-specific computational model of cardiac electrophysiology is updated based on the additional intra-operative patient-specific measurements. The patient-specific computational model of cardiac electrophysiology is updated by re-estimating the patient-specific computational model of cardiac electrophysiology based on the registered patient-specific anatomical model and the additional patient-specific measurements using the method of FIG. 6. Once the patient-specific computational model of cardiac electrophysiology is updated, additional virtual pacing may be performed, and updated abalation site guidance maps (ASGM) are generated. Since embodiments of the present invention utilize the computationally efficient LBM-EP technique for solving the cardiac electrophysiology model, the ASGM can be updated in real-time or near real-time in response to additional intraoperative measurements acquired during the intervention.

At step 218, if it is determined at step 214 that an ablation target has been identified, the electrophysiologist performs the ablation at the identified ablation target, and the planning and guidance method of FIG. 2 can terminate.

Figure 9:
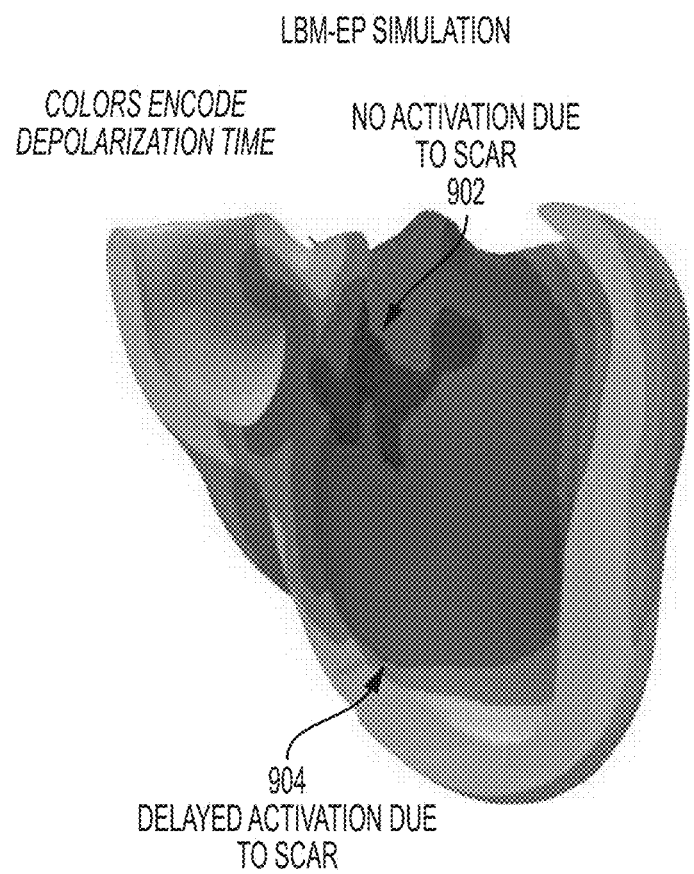
FIG. 9 illustrates an exemplary depolarization map computed from an anatomical model of a patient with a septal scar due to surgery of hypertrophic cardiomyopathy.

FIG. 9 illustrates an exemplary depolarization map computed from an anatomical model of a patient with a septal scar due to surgery of hypertrophic cardiomyopathy. The depolarization map of FIG. 9 includes a region 902 in which there is no activation due to the scar and a region 904 in which there is delayed activation due to the scar. As shown in FIG. 9, the cardiac electrophysiology has been computed throughout the entire myocardium. Hence, by combining imaging, ECG and endocardial mapping together, the above described methods allow mid-wall or epicardial VT circuits not directly accessible through endocardial mapping only to be accessed.

Figure 10:
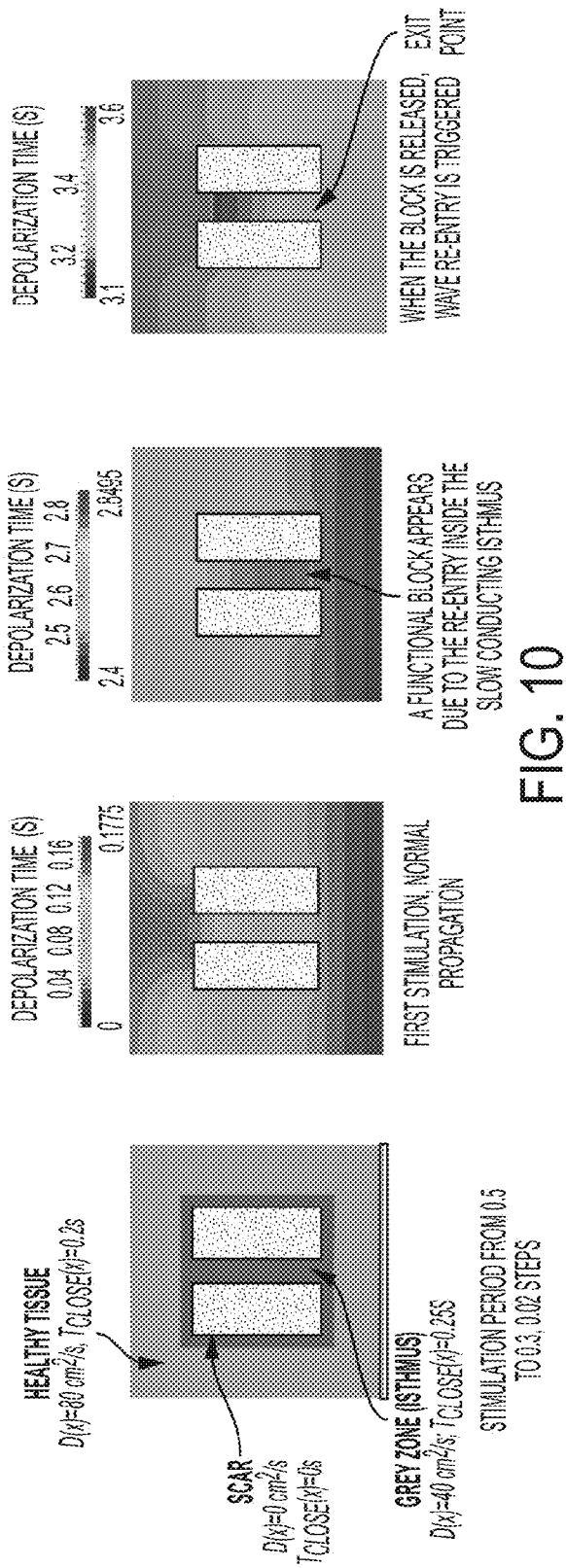
FIG. 10 illustrates exemplary results obtained by applying the methods of FIGS. 2 and 6 with a synthetic geometry.

FIG. 10 illustrates exemplary results obtained by applying the methods of FIGS. 2 and 6 with a synthetic geometry. This experiment was carried out on a 10 cm×10 cm×3 mm slab of healthy cardiac tissue, which contains at its center a scar with a thin isthmus of border zone tissue. The slab is paced at the bottom at a linearly increasing pacing frequency. Ratios between border zone parameters and healthy parameters were taken from the literature. The first "beats" were regular, although the electrical front was propagating significantly slower within the isthmus. This phenomenon, in conjunction with the increased APD in that area, which mimics a modified restitution curve, led to a functional block as soon as the fast propagating lateral wave could enter the isthmus from the top. As the functional block faded away, the electrical wave could exit from the bottom of the isthmus, thus generating a wave re-entry susceptible of triggering VT. This experiment demonstrates the ability of the above described methods to capture post MI VT.

Figure 11:
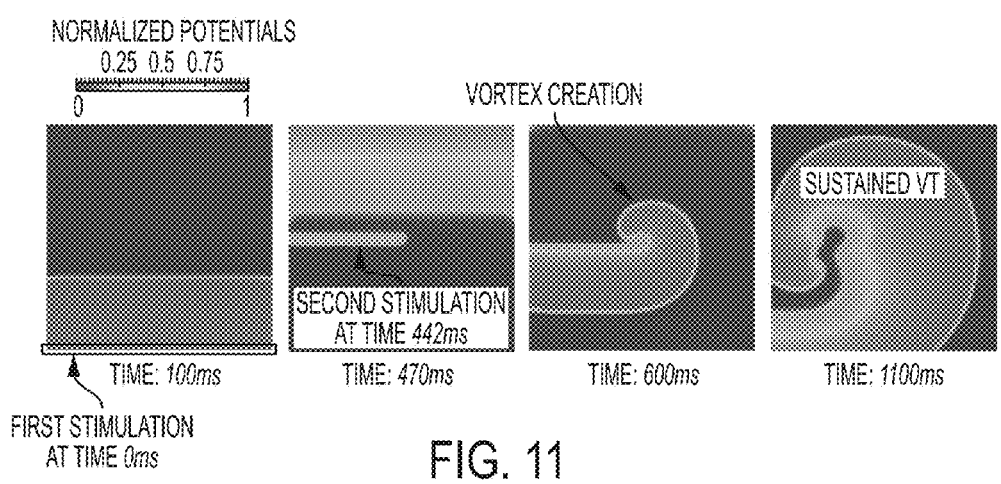
FIG. 11 illustrates exemplary results that capture VT due to ectopic regions.

FIG. 11 illustrates exemplary results that capture VT due to ectopic regions. In this experiment, the cardiac electrophysiology resulting from an early stimulation at the center of the domain was computed. Due to the preceding front, the second electrical wave could propagate only backwards and eventually started to loop around itself as the cells repolarized. A re-entry appeared, resulting in sustained vortices susceptible of triggering VT. This experiment demonstrates the ability of the above described methods to capture VT due to ectopic regions.

Although the methods described above discuss ablation therapy for VT or VF, the present invention is not limited thereto. Embodiments of the present invention can be similarly applied for planning and guidance of ablation therapy related to other electrophysiology troubles, such as atrial fibrillation, Wolff-Parkinson-White disease, etc. Furthermore, the present invention is not limited to any particular ablation technology, and embodiments of the present invention can be used with various types of ablation technology, such as radiofrequency ablation, cryo-ablation, high intensity focused ultrasound (HIFU), etc.

In addition to the techniques described above, embodiments of the present invention can use body surface potential mapping and reconstructed epicardial maps based on torso measurements to estimate ASGM. Body surface mapping can be used alone or in addition to the endocardial mapping and/or ECG for improved accuracy.

According to an embodiment of the present invention, ranges of physiological parameters (diffusivity, APD, etc.) can be learned from data related to various patients and used to better initialize the estimation process. These ranges can be updated in real time and adapted to the patient during the intervention, as more data is acquired. Further, according to an embodiment of the present invention, a manifold of ASGM can be learned from the data acquired in a population. Statistical methods can be used to learn the factors underlying the observed ASGM. The manifold can then be used as a constrained space to compute new ASGM of new patients. The learned manifold can also be used to reduce estimation ambiguity when several solutions are found for a given set of measurements.

In an embodiment of the present invention, model parameters of the cardiac electrophysiology model can be modifies according to drugs currently taken by the patient. In an embodiment of the present invention, different ablation strategies can be tested in-silico by locally disrupting tissue properties at the targeted ablation sites (e.g., decreases tissue conductivity, etc.).

Figure 12:
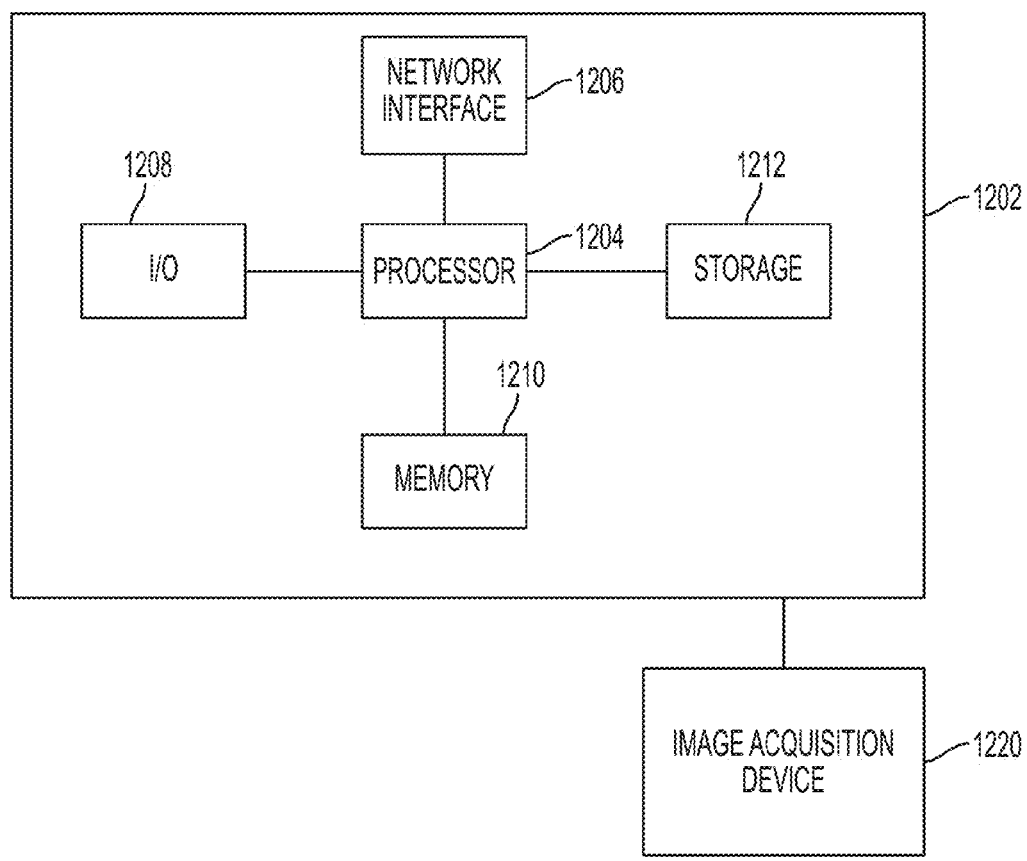
FIG. 12 is a high-level block diagram of a computer capable of implementing the present invention.

The above-described methods for patient-specific planning and guidance of ablative procedures for cardiac arrhythmias, generating a patient-specific anatomic model of the heart, and estimating a patient-specific computational model of cardiac electrophysiology and generating ablation site guidance maps for a patient according to an embodiment of the present invention can be implemented on a computer using well-known computer processors, memory units, storage devices, computer software, and other components. A high-level block diagram of such a computer is illustrated in FIG. 12. Computer 1202 contains a processor 1204, which controls the overall operation of the computer 1202 by executing computer program instructions which define such operation. The computer program instructions may be stored in a storage device 1212 (e.g., magnetic disk) and loaded into memory 1210 when execution of the computer program instructions is desired. Thus, the steps of the methods of FIGS. 1, 2, 3, and 6 may be defined by the computer program instructions stored in the memory 1210 and/or storage 1212 and controlled by the processor 1204 executing the computer program instructions. An image acquisition device 1220, such as a CT scanning device, C-arm image acquisition device, MR scanning device, Ultrasound device, etc., can be connected to the computer 1202 to input image data to the computer 1202. It is possible to implement the image acquisition device 1220 and the computer 1202 as one device. It is also possible that the image acquisition device 1220 and the computer 1202 communicate wirelessly through a network. The computer 1202 also includes one or more network interfaces 1206 for communicating with other devices via a network. The computer 1202 also includes other input/output devices 1208 that enable user interaction with the computer 1202 (e.g., display, keyboard, mouse, speakers, buttons, etc.). Such input/output devices 1208 may be used in conjunction with a set of computer programs as an annotation tool to annotate volumes received from the image acquisition device 1220. One skilled in the art will recognize that an implementation of an actual computer could contain other components as well, and that FIG. 12 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for patient-specific guidance of an ablation procedure, comprising:
    registering a patient-specific anatomical heart model extracted from pre-operative cardiac image data to a coordinate system of an intra-operative image acquired during the ablation procedure;
    estimating a patient-specific computational model of cardiac electrophysiology based on the registered patient-specific anatomical heart model and intra-operative patient-specific measurements acquired during the ablation procedure; and
    generating one or more ablation site guidance maps based on the patient-specific computational model of cardiac electrophysiology.

2. The method of claim 1, further comprising:
    displaying the one or more ablation site guidance maps on a display device during the ablation procedure.

3. The method of claim 1, further comprising:
receiving the pre-operative cardiac image data; and
generating the patient-specific anatomical heart model based on the pre-operative cardiac image data.

4. The method of claim 3, wherein generating the patient-specific anatomical heart model based on the pre-operative cardiac image data comprises:
extracting a multi-component patient-specific heart morphology model from the pre-operative cardiac image data;
fusing the multi-component patient-specific heart morphology model into a single heart model and tagging surface elements of the single heart model into surface zones; and
generating a model of myocardium fiber architecture based on the single heart model.

5. The method of claim 4, wherein generating the patient-specific anatomical heart model based on the pre-operative cardiac image data further comprises:
segmenting scar tissue in the pre-operative image data; and
mapping the segmented scar tissue to the volumetric single heart model.

6. The method of claim 1, wherein registering a patient-specific anatomical heart model extracted from pre-operative cardiac image data to a coordinate system of an intra-operative image acquired during the ablation procedure comprises:
registering the patient-specific anatomical heart model to an intra-operative three-dimensional rotational angiography image acquired during the ablation procedure.

7. The method of claim 6, wherein registering the patient-specific anatomical heart model to an intra-operative three-dimensional rotational angiography image acquired during the ablation procedure comprises:
calculating a probability map of a cardiac pericardium in the three-dimensional rotational angiography image using a machine learning algorithm;
calculating a deformation that maps the pericardium surface mesh of the patient-specific anatomical heart model to the coordinate system of the three-dimensional rotational angiography image using an optimization algorithm that maximizes the probability map along the surface mesh;
calculating a dense deformation field by extrapolating the deformation of every node;
registering the patient-specific anatomical heart model to the coordinate system of the three-dimensional rotational angiography image using the dense deformation field; and
re-orienting myocardium fibers of the patient-specific anatomical heart model using a local Jacobian matrix of the dense deformation field.

8. The method of claim 1, wherein registering a patient-specific anatomical heart model extracted from pre-operative cardiac image data to a coordinate system of an intra-operative image acquired during the ablation procedure comprises:
registering the patient-specific anatomical heart model to the coordinate system of the intra-operative image based on spatial fiducials provided in the intra-operative image by an endocardial mapping system.

9. The method of claim 1, wherein registering a patient-specific anatomical heart model extracted from pre-operative cardiac image data to a coordinate system of an intra-operative image acquired during the ablation procedure comprises:
calculating a transformation to register a component of the patient-specific anatomical heart model to the coordinate system of the intra-operative image; and
transforming the patient-specific anatomical entire heart model using the calculated transformation.

10. The method of claim 1, wherein estimating a patient-specific computational model of cardiac electrophysiology based on the registered patient-specific anatomical heart model and intra-operative patient-specific measurements acquired during the ablation procedure comprises:
generating a Cartesian grid domain using the registered patient-specific anatomical heart model; and
calculating transmembrane potential variation over time at each of a plurality of nodes within the myocardium in the Cartesian grid domain by computing a solution of a cardiac electrophysiology model for each of the plurality of nodes using a Lattice-Boltzmann method for electrophysiology.

11. The method of claim 10, wherein estimating a patient-specific computational model of cardiac electrophysiology based on the registered patient-specific anatomical heart model and intra-operative patient-specific measurements acquired during the ablation procedure further comprises:
estimating parameters of the cardiac electrophysiology model using an inverse problem approach.

12. The method of claim 11, wherein estimating parameters of the cardiac electrophysiology model using an inverse problem approach comprises:
calculating a cost function that compares the depolarization and repolarization times calculated the plurality of nodes using the cardiac electrophysiology model with depolarization and repolarization times determined from current intra-operative electrophysiological mapping measurements of the patient acquired during the ablation procedure;
estimating electrical diffusivity and action potential duration parameters of the cardiac electrophysiology model using an inverse problem algorithm to minimize the cost function; and
re-calculating the transmembrane potential variation over time at each of the plurality of nodes within the myocardium in the Cartesian grid domain by computing a solution of a cardiac electrophysiology model with the fitted diffusivity and action potential duration parameters for each of the plurality of nodes using the Lattice-Boltzmann method for electrophysiology.

13. The method of claim 1, further comprising:
performing virtual pacing using the patient-specific computational model of cardiac electrophysiology.

14. The method of claim 13, wherein generating one or more ablation site guidance maps based on the patient-specific computational model of cardiac electrophysiology comprises:
generating one or more ablation site guidance maps based on the patient-specific computational model of cardiac electrophysiology and the virtual pacing.

15. The method of claim 14, wherein generating one or more ablation site guidance maps based on the patient-specific computational model of cardiac electrophysiology and the virtual pacing comprises:
generating the one or more ablation site guidance maps resulting from a computation of cardiac electrophysiology in response to the virtual pacing using the patient-specific computational model of cardiac electrophysiology.

16. The method of claim 14, wherein generating one or more ablation site guidance maps based on the patient-specific computational model of cardiac electrophysiology and the virtual pacing comprises:

generating a map of ventricular tachycardia (VT) trigger point candidates based on the virtual pacing.

17. The method of claim 13, wherein performing virtual pacing using the patient-specific computational model of cardiac electrophysiology comprises:
   receiving a user selection of a spatial location of a virtual pacing catheter; and
   calculating potential variation over time at a plurality of points within the myocardium using the patient-specific computational model of cardiac electrophysiology with a stimulus current added at the selected spatial location and applied at a user-defined frequency.

18. The method of claim 13, wherein performing virtual pacing using the patient-specific computational model of cardiac electrophysiology comprises:
   automatically selecting a plurality of spatial locations at which to perform virtual pacing; and
   for each of the plurality of spatial locations, calculating potential variation over time at a plurality of points within the myocardium using the patient-specific computational model of cardiac electrophysiology with a stimulus current added at that spatial location and applied at one or more different frequencies.

19. The method of claim 1, wherein generating one or more ablation site guidance maps based on the patient-specific computational model of cardiac electrophysiology comprises:
   generating three-dimensional maps of one or more fitted parameters of the patient-specific computational model of cardiac electrophysiology over a spatial domain defined using the registered patient-specific anatomical heart model.

20. The method of claim 19, wherein generating three-dimensional maps of one or more fitted parameters of the patient-specific computational model of cardiac electrophysiology over a spatial domain defined using the registered patient-specific anatomical heart model comprises:
   generating a three-dimensional map of a tissue diffusivity parameter at each of a plurality of nodes of the spatial domain; and
   generating a three-dimensional map of an action potential duration parameter at each of the plurality of nodes of the spatial domain.

21. The method of claim 1, wherein generating one or more ablation site guidance maps based on the patient-specific computational model of cardiac electrophysiology comprises:
   generating a time varying three-dimensional map of potentials of the plurality of nodes based on the patient-specific computational model of cardiac electrophysiology;
   generating a three-dimensional map of depolarization times of the plurality of nodes based on the time varying three-dimensional map of potentials; and
   generating a three-dimensional map of repolarization times of the plurality of nodes based on the time varying three-dimensional map of potentials.

22. The method of claim 1, further comprising:
   acquiring additional intra-operative patient-specific measurements during the ablation procedure;
   updating the patient-specific computational model of cardiac electrophysiology based on the registered patient-specific anatomical heart model and the additional intra-operative patient-specific measurements acquired during the ablation procedure; and
   re-generating the one or more ablation site guidance maps based on the updated patient-specific computational model of cardiac electrophysiology.

23. An apparatus for patient-specific guidance of an ablation procedure, comprising:
   means for registering a patient-specific anatomical heart model extracted from pre-operative cardiac image data to a coordinate system of an intra-operative image acquired during the ablation procedure;
   means for estimating a patient-specific computational model of cardiac electrophysiology based on the registered patient-specific anatomical heart model and intra-operative patient-specific measurements acquired during the ablation procedure; and
   means for generating one or more ablation site guidance maps based on the patient-specific computational model of cardiac electrophysiology.

24. The apparatus of claim 23, further comprising:
   means for displaying the one or more ablation site guidance maps on a display device during the ablation procedure.

25. The apparatus of claim 23, further comprising:
   means for generating the patient-specific anatomical heart model based on the pre-operative cardiac image data.

26. The apparatus of claim 23, wherein the means for estimating a patient-specific computational model of cardiac electrophysiology based on the registered patient-specific anatomical heart model and intra-operative patient-specific measurements acquired during the ablation procedure comprises:
   means for generating a Cartesian grid domain using the registered patient-specific anatomical heart model; and
   means for calculating transmembrane potential variation over time at each of a plurality of nodes within the myocardium in the Cartesian grid domain by computing a solution of a cardiac electrophysiology model for each of the plurality of nodes using a Lattice-Boltzmann method for electrophysiology.

27. The apparatus of claim 26, wherein the means for estimating a patient-specific computational model of cardiac electrophysiology based on the registered patient-specific anatomical heart model and intra-operative patient-specific measurements acquired during the ablation procedure further comprises:
   means for estimating parameters of the cardiac electrophysiology model using an inverse problem approach.

28. The apparatus of claim 27, wherein the means for estimating parameters of the cardiac electrophysiology model using an inverse problem approach comprises:
   means for calculating a cost function that compares the depolarization and repolarization times calculated the plurality of nodes using the cardiac electrophysiology model with depolarization and repolarization times determined from current intra-operative electrophysiological mapping measurements of the patient acquired during the ablation procedure;
   means for estimating electrical diffusivity and action potential duration parameters of the cardiac electrophysiology model using an inverse problem algorithm to minimize the cost function; and
   means for re-calculating the transmembrane potential variation over time at each of the plurality of nodes within the myocardium in the Cartesian grid domain by computing a solution of a cardiac electrophysiology model with the fitted diffusivity and action potential duration parameters for each of the plurality of nodes using the Lattice-Boltzmann method for electrophysiology.

29. The apparatus of claim 23, further comprising:
means for performing virtual pacing using the patient-specific computational model of cardiac electrophysiology.

30. The apparatus of claim 29, wherein the means for generating one or more ablation site guidance maps based on the patient-specific computational model of cardiac electrophysiology comprises:
means for generating one or more ablation site guidance maps based on the patient-specific computational model of cardiac electrophysiology and the virtual pacing.

31. The apparatus of claim 23, further comprising:
means for acquiring additional intra-operative patient-specific measurements during the ablation procedure;
means for updating the patient-specific computational model of cardiac electrophysiology based on the registered patient-specific anatomical heart model and the additional intra-operative patient-specific measurements acquired during the ablation procedure; and
means for re-generating the one or more ablation site guidance maps based on the updated patient-specific computational model of cardiac electrophysiology.

32. The non-transitory computer readable medium of claim 31, wherein generating one or more ablation site guidance maps based on the patient-specific computational model of cardiac electrophysiology comprises:
generating three-dimensional maps of one or more fitted parameters of the patient-specific computational model of cardiac electrophysiology over a spatial domain defined using the registered patient-specific anatomical heart model.

33. The non-transitory computer readable medium of claim 32, wherein generating three-dimensional maps of one or more fitted parameters of the patient-specific computational model of cardiac electrophysiology over a spatial domain defined using the registered patient-specific anatomical heart model comprises:
generating a three-dimensional map of a tissue diffusivity parameter at each of a plurality of nodes of the spatial domain; and
generating a three-dimensional map of an action potential duration parameter at each of the plurality of nodes of the spatial domain.

34. A non-transitory computer readable medium storing computer program instructions for patient-specific guidance of an ablation procedure, the computer program instructions when executed by a processor cause the processor to perform operations comprising:
registering a patient-specific anatomical heart model extracted from pre-operative cardiac image data to a coordinate system of an intra-operative image acquired during the ablation procedure;
estimating a patient-specific computational model of cardiac electrophysiology based on the registered patient-specific anatomical heart model and intra-operative patient-specific measurements acquired during the ablation procedure; and
generating one or more ablation site guidance maps based on the patient-specific computational model of cardiac electrophysiology.

35. The non-transitory computer readable medium of claim 34, wherein the operations further comprise:
displaying the one or more ablation site guidance maps on a display device during the ablation procedure.

36. The non-transitory computer readable medium of claim 34, wherein the operations further comprise:
receiving the pre-operative cardiac image data; and
generating the patient-specific anatomical heart model based on the pre-operative cardiac image data.

37. The non-transitory computer readable medium of claim 34, wherein estimating a patient-specific computational model of cardiac electrophysiology based on the registered patient-specific anatomical heart model and intra-operative patient-specific measurements acquired during the ablation procedure comprises:
generating a Cartesian grid domain using the registered patient-specific anatomical heart model; and
calculating transmembrane potential variation over time at each of a plurality of nodes within the myocardium in the Cartesian grid domain by computing a solution of a cardiac electrophysiology model for each of the plurality of nodes using a Lattice-Boltzmann method for electrophysiology.

38. The non-transitory computer readable medium of claim 37, wherein estimating a patient-specific computational model of cardiac electrophysiology based on the registered patient-specific anatomical heart model and intra-operative patient-specific measurements acquired during the ablation procedure further comprises:
estimating parameters of the cardiac electrophysiology model using an inverse problem approach.

39. The non-transitory computer readable medium of claim 38, wherein estimating parameters of the cardiac electrophysiology model using an inverse problem approach comprises:
calculating a cost function that compares the depolarization and repolarization times calculated the plurality of nodes using the cardiac electrophysiology model with depolarization and repolarization times determined from current intra-operative electrophysiological mapping measurements of the patient acquired during the ablation procedure;
estimating electrical diffusivity and action potential duration parameters of the cardiac electrophysiology model using an inverse problem algorithm to minimize the cost function; and
re-calculating the transmembrane potential variation over time at each of the plurality of nodes within the myocardium in the Cartesian grid domain by computing a solution of a cardiac electrophysiology model with the fitted diffusivity and action potential duration parameters for each of the plurality of nodes using the Lattice-Boltzmann method for electrophysiology.

40. The non-transitory computer readable medium of claim 34, wherein the operations further comprise:
performing virtual pacing using the patient-specific computational model of cardiac electrophysiology.

41. The non-transitory computer readable medium of claim 40, wherein generating one or more ablation site guidance maps based on the patient-specific computational model of cardiac electrophysiology comprises:
generating one or more ablation site guidance maps based on the patient-specific computational model of cardiac electrophysiology and the virtual pacing.

42. The non-transitory computer readable medium of claim 41, wherein generating one or more ablation site guidance maps based on the patient-specific computational model of cardiac electrophysiology and the virtual pacing comprises:
generating a map of ventricular tachycardia (VT) trigger point candidates based on the virtual pacing.

43. The non-transitory computer readable medium of claim 40, wherein performing virtual pacing using the patient-specific computational model of cardiac electrophysiology comprises:
receiving a user selection of a spatial location of a virtual pacing catheter; and
calculating potential variation over time at a plurality of points within the myocardium using the patient-specific computational model of cardiac electrophysiology with a stimulus current added at the selected spatial location and applied at a user-defined frequency.

44. The non-transitory computer readable medium of claim 40, wherein performing virtual pacing using the patient-specific computational model of cardiac electrophysiology comprises:
   automatically selecting a plurality of spatial locations at which to perform virtual pacing; and
   for each of the plurality of spatial locations, calculating potential variation over time at a plurality of points within the myocardium using the patient-specific computational model of cardiac electrophysiology with a stimulus current added at that spatial location and applied at one or more different frequencies.

45. The non-transitory computer readable medium of claim 34, wherein the operations further comprise:
   acquiring additional intra-operative patient-specific measurements during the ablation procedure;
   updating the patient-specific computational model of cardiac electrophysiology based on the registered patient-specific anatomical heart model and the additional intra-operative patient-specific measurements acquired during the ablation procedure; and
   re-generating the one or more ablation site guidance maps based on the updated patient-specific computational model of cardiac electrophysiology.

* * * * *